United States Patent [19]

Abou-Gharbia

[11] Patent Number: 4,892,943
[45] Date of Patent: Jan. 9, 1990

[54] FUSED BICYCLIC IMIDES WITH PSYCHOTROPIC ACTIVITY

[75] Inventor: Magid A. Abou-Gharbia, Wilmington, Del.

[73] Assignee: American Home Products Corporation, New York, N.Y.

[21] Appl. No.: 237,106

[22] Filed: Aug. 26, 1988

Related U.S. Application Data

[63] Continuation-in-part of Ser. No. 909,049, Sep. 18, 1986, abandoned, which is a continuation-in-part of Ser. No. 892,160, Jul. 30, 1986, abandoned, which is a continuation-in-part of Ser. No. 787,887, Oct. 16, 1985, abandoned.

[51] Int. Cl.[4] ................. A61K 31/495; C07D 401/06; C07D 401/14
[52] U.S. Cl. ..................................... 540/575; 544/234; 544/238; 544/239; 544/295; 544/300; 544/357; 544/360; 544/364; 544/372
[58] Field of Search .............. 544/295, 357, 257, 405, 544/234, 238, 239, 300, 360, 364, 372

[56] References Cited

U.S. PATENT DOCUMENTS 2,562,255 12/1985 Freed et al. ..................... 544/405
4,804,751 2/1989 Abou-Gharbia ................. 540/575

FOREIGN PATENT DOCUMENTS 0200968 12/1986 European Pat. Off. ............ 544/360

*Primary Examiner*—William R. Dixon, Jr.
*Assistant Examiner*—Miriam Sohn
*Attorney, Agent, or Firm*—George Tarnowski

[57] ABSTRACT

There are disclosed compounds of the formula

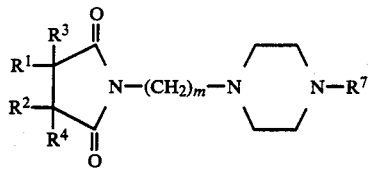

wherein
$R^1$ and $R^2$ represent the structure

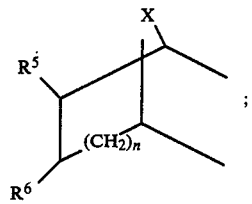

$R^3$ and $R^4$ are hydrogen, or $R^3$ and $R^4$ taken together form a 3-5 membered saturated carbocyclic ring;
$R^5$ and $R^6$ are hydrogen, or $R^5$ and $R^6$ taken together form a 3-6 membered carbocyclic ring or a cyclobutenyl ring; with the proviso that when $R^3$, $R^4$, $R^5$ and $R^6$ are hydrogen, n is other than zero;
m is 2-4;
n is 0-4;
X is lower alkylene, vinylene or O;
$R^7$ is unsubstituted or substituted phenyl, 2-pyridinyl, 2-pyrimidinyl, 2-pyrazinyl or 3-pyridazinyl; where the substituents are selected from the group lower alkyl, lower alkoxy, halo, cyano, nitro and trifluoromethyl;
and the pharmaceutically acceptable salts thereof and their use as antipsychotic/anxiolytic agents having a low liability for extrapyramidal side effects.

34 Claims, No Drawings

FUSED BICYCLIC IMIDES WITH PSYCHOTROPIC ACTIVITY

This application is a continuation-in-part of U.S. Ser. No. 909,049, filed September 18, 1986, now abandoned which is a continuation-in-part of U.S. Ser. No. 892,160, filed July 30, 1986, now abandoned, which is a continuation-in-part of U.S. Ser. No. 787,887, filed October 16, 1985, now abandoned.

This invention relates to novel compounds having antipsychotic, anxiolytic and antidepressant activity and being characterized by the general formula

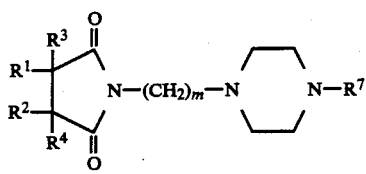

wherein
$R^1$ and $R^2$ represent the structure

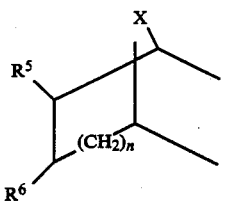

$R^3$ and $R^4$ are hydrogen, or $R^3$ and $R^4$ taken together form a 3–5 membered saturated carbocyclic ring;
$R^5$ and $R^6$ are hydrogen or $R^5$ and $R^6$ taken together form a 3–6 membered carbocyclic ring or a cyclobutenyl ring; with the proviso that when $R^3$, $R^4$, $R^5$ and $R^6$ are hydrogen, n is other than zero;
m is 2–4;
n is 0–4;
X is lower alkylene, vinylene or O;
$R^7$ is unsubstituted or substituted phenyl, 2-pyridinyl, 2-pyrimidinyl, 2-pyrazinyl or 3-pyridazinyl; where the substituents are selected from the group lower alkyl, lower alkoxy, halo, cyano, nitro and trifluoromethyl;
and the pharmaceutically acceptable salts thereof.

The term "lower alkyl" refers to moieties having 1–6 carbon atoms in the carbon chain. The term "lower alkylene" refers to moieties having 1–4 carbon atoms in the carbon chain. The term "alkoxy" refers to moieties having 1–6 carbon atoms. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. Thus, the compounds can be prepared, for example, by reacting maleimide with an appropriate diene, e.g. 1,3,5,7-cyclooctatetraene, to yield a precursor which when reacted with a suitable dihalo lower alkane affords an intermediate product:

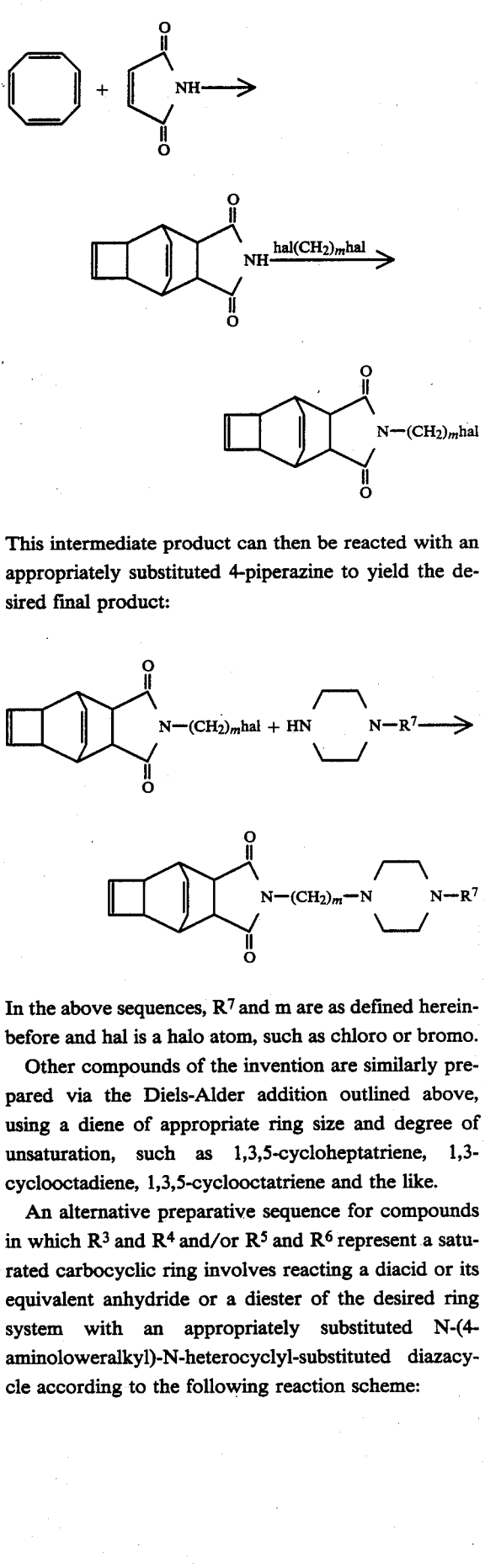

In the above sequences, $R^7$ and m are as defined hereinbefore and hal is a halo atom, such as chloro or bromo.

Other compounds of the invention are similarly prepared via the Diels-Alder addition outlined above, using a diene of appropriate ring size and degree of unsaturation, such as 1,3,5-cycloheptatriene, 1,3-cyclooctadiene, 1,3,5-cyclooctatriene and the like.

An alternative preparative sequence for compounds in which $R^3$ and $R^4$ and/or $R^5$ and $R^6$ represent a saturated carbocyclic ring involves reacting a diacid or its equivalent anhydride or a diester of the desired ring system with an appropriately substituted N-(4-aminoloweralkyl)-N-heterocyclyl-substituted diazacycle according to the following reaction scheme:

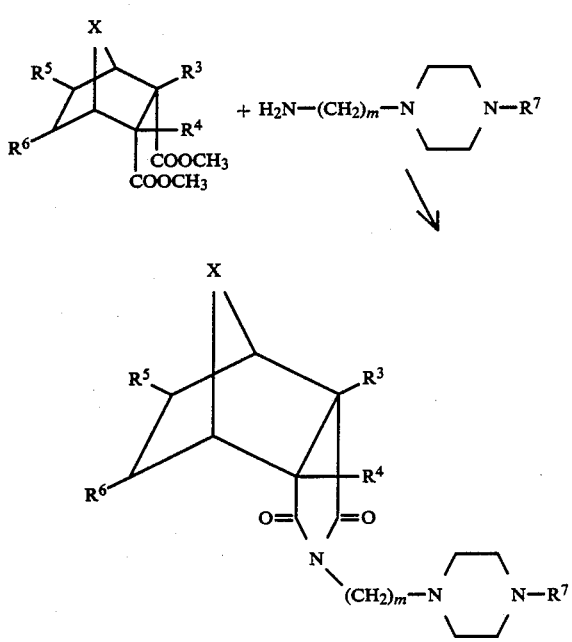

In an alternative preparative sequence, maleimide can first be reacted with a dihalo lower alkane followed by reaction with an appropriately substituted diazacycle to yield the following intermediate:

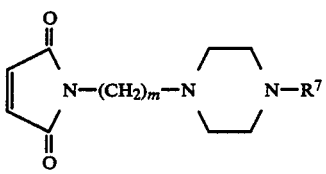

which can then be further subjected to Diels-Alder addition with appropriate reactants to yield desired final products.

The saturated analogs of the compounds discussed in all of the previous preparative schemes can be prepared by hydrogenating the intermediates or the final products using hydrogen and Pd/C as a catalyst.

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]-butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses.

Further, the compounds of the invention demonstrate an antagonist profile when tested for their activity as ligands for the 5-HT$_{1A}$ receptor. Evidence exists that a reduction in serotonergic activity by blockade of 5-HT$_{1A}$ receptors correlates with anxiolytic drug activity. Thus, anxiolytic drugs such as buspirone and ipsapirone have been found to be mixed agonists/antagonists of the 5-HT$_{1A}$ behavioral syndrome [see Smith and Peroutka, *Pharmacol Biochem Behav.*, 24, 1513–19 (1986)], which is a measure of the post-synaptic efficacy of compounds with an affinity for the 5-HT$_{1A}$ receptor subtype. The results of such testing have relevance in the prediction of anxiolytic activity of the compounds tested. While buspirone exhibits a mixed agonist/antagonist profile with respect to activity at the 5-HT$_{1A}$ receptor site, compounds such as 8-[2-[(2,3-dihydro-1,4-benzodioxin-2-yl]methylamino]ethyl]-8-azaspiro[4,5]decan-7,9-dione methane sulfonate (MDL 73005 SEF) and 8-[4-[4-(2-methoxyphenyl)-1-piperazinyl]ethyl]-8-azaspiro[4,5]-decane-7,9-dione (BMY-7378) display a clear antagonist profile. Compounds of the invention display a profile more nearly like MDL 73005 SEF and BMY-7378, rather than like buspirone when tested for 5-HT$_{1A}$ receptor site activity, indicating that they act as 5-HT$_{1A}$ antagonists.

When employed as anxiolytics/antipsychotics, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/anti-psychotic agents, they can be formulated into oral dosage forms such as tablets, capsules and the like. The compounds can be administered alone or by combining them with conventional carriers, such as magnesium carbonate, magnesium sterate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic and anxiolytic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

2-[4-[4-(6-Chloro-2-pyrazinyl)-1-piperazinyl]butyl]hexahydro-4,6-ethenocycloprop[f]isoindole-1,3(2H,3aH)-dione, dihydrochloride, sesquihydrate To a stirred solution of 6.8 g (0.035 mol) of 1,3-dioxo-2H-4,6-etheno-1,3,3a,6a-tetrahydrocycloprop[f]isoindole in 70 mL of dimethylformamide is added 0.9 g of sodium hydride. The suspension is stirred at 60° C. for 3 hours and is poured into a stirred solution of 1,4-dibromobutane (9 g, 0.04 mol) in 50 mL of dimethylformamide.

The reaction mixture is stirred at room-temperature for 24 hours, dimethylformamide is evaporated under reduced pressure and the residue is extracted with methylene chloride (3×200 mL). The methylene chloride extracts are collected, washed with water, dried over anhydrous $Na_2SO_4$ and evaporated under reduced pressure. The residue is solidified to a waxy like material affording 7.6 g (67% yield) of the corresponding 2-(4-bromobutyl)-hexahydro-4,6-ethenocycloprop[f]isoindole-1,3(2H,3aH)-dione. The title compound is prepared by dissolving 2.5 g (0.007 mole) of 2-(4-bromobutylhexahydro-4,6-ethenocycloprop[f]isoindole-1,3(2H,3aH)-dione in 50 mL of dimethylformamide, and to this solution is added 6 mL of triethylamine and 1.7 g (0.007 mL) of 1-(6-chloro-2-pyrazinyl)-piperazine hydrochloride. The reaction mixture is stirred at room temperature for 48 hours. Dimethylformamide is removed under reduced pressure and the remaining solid is extracted with 2×100 mL of methylene chloride.

The methylene chloride extracts are dried over anhydrous $Na_2SO_4$, evaporated and the title compound is separated by HPLC using 30% methanolethyl acetate as eluent. Evaporation of the solvent from the desired fractions ($R_f$ 0.5) affords 0.95 g (31% yield) of the title compound which is converted to the dihydrochloride salt by dissolving the free base in ethanol and adding ether saturated with hydrogen chloride; m.p. 258°–261° C.

Analysis for: $C_{23}H_{28}ClN_5O_2.2HCl.1\frac{1}{2}H_2O$: Calculated: C, 50.96; H, 6.09; N, 12.92. Found: C, 50.90; H, 6.09; N, 13.09.

EXAMPLE 2

4,4a,5,5a,6,6a-Hexahydro-2-[4-[4-(2-pyrimidinyl)-1-piperazinyl]butyl]-4,6-ethenocycloprop[f]isoindole-1,3-(2H,3aH)-dione,dihydrochloride The title compound is prepared following the procedure of Example 1 using 1-(2-pyrimidinyl)piperazine dihydrochloride instead of 1-(6-chloro-2-pyrazinyl)piperazine hydrochlorde and is converted to the dihydrochloride salt; m.p. 207°–208° C.

Analysis for: $C_{23}H_{29}N_5O_2.2HCl.H_2O$: Calculated: C, 55.42; H, 6.62; N, 14.0; C, 14.25. Found: C, 54.92; H, 6.42; N, 13.60; Cl, 14.38.

EXAMPLE 3

3a,4,4a,6a,7,7a-Hexahydro-2-[4-[4-(2-pyrimidinyl)-1-piperazinyl]butyl]-4,7-etheno-1H-cyclobut[f]isoindole-1,3(2H)-dione, dihydrochloride, sesquihydrate The title compound is prepared following the procedure of Example 1, using 1,3-dioxo-4,7-etheno-$\Delta^5$-1,3,3a,7a-tetrahydrocyclobut[f]isoindole instead of 1,3-dioxo-2H-4,6-etheno-1,3,3a,6a-tetrahydrocycloprop[f]isoindole, and 1-(2-pyrimidinyl)piperazine instead of 1-(6-chloro-2-pyrazinyl)-piperazine. The compound is converted to the dihydrochloride salt; m.p. 252°–254° C.

Analysis for: $C_{24}H_{29}N_5O_2.2HCl.1\frac{1}{2}H_2O$: Calculated: C, 55.44; H, 6.54; N, 13.48. Found: C, 55.00; H, 6.28; N, 13.27.

EXAMPLE 4

3a,4,4a,6a,7,7a-Hexahydro-2-[4-[4-(6-chloro-2-pyrazinyl)-1-piperazinyl]butyl]-4,7-etheno-1H-cyclobut[f]isoindole-1,3(2H)-dione, dihydrochloride, sesquihydrate The title compound is prepared following the procedure of Example 1 using 1-(6-chloro-2-pyrazinyl)piperazine hydrochloride instead of 1-(2-pyrimidyl)piperazine dihydrochloride and 1,3-dioxo-4,7-etheno-$\Delta^5$-1,3,3a,7a-tetrahydrocyclobut[f]isoindole instead of 1,3-dioxo-2H-4,6-etheno-1,3,3a,6a-tetrahydrocycloprop[f]isoindole. The compound is converted to the dihydrochloride salt; m.p. >300° C.

Analysis for: $C_{24}H_{28}ClN_5O_2.2HCl.1\frac{1}{2}H_2O$: Calculated: C, 52.03; H, 6.0; N, 12.64. Found: C, 51.85; H, 5.74; N, 12.59.

EXAMPLE 5

2-[4-[4-(6-Chloro-2-pyrazinyl-1-piperazinyl]butyl]-octahydroo-4,7-ethano-1H-cyclobut[f]isoindole-1,3-(2H)-dione, hydrochloride, hemihydrate The title compound is prepared following the procedure of Example 1 using 1,3-dioxo-4,7-ethano-1,3,3a,7a-tetrahydrocyclobut[f]isoindole instead of 1,3-dioxo-4,6-etheno-1,3,3a,6a-tetrahydrocycloprop[f]isoindole and is converted to the hydrochloride salt; m.p. 273°–275° C.

Analysis for: $C_{24}H_{32}ClN_5O_2.HCl.\frac{1}{2}H_2O$: Calculated: C, 57.25; H, 6.56; N, 13.91. Found: C, 56.91; H, 6.41; N, 13.80.

EXAMPLE 6

2-[4-[4-(2-Pyrimidinyl)-1-piperazinyl]butyl]octahydro-4,7ethano-1H-cyclobut[f]isoindole-1,3-(2H)-dione, dihydrochloride, sesquihydrate The title compound is prepared following the procedure of Example 1 using 1-(2-pyrimidinyl)piperazine dihydrochloride instead of 1-(6-chloro-2-pyrazinyl)piperazine hydrochloride and 1,3-dioxo-4,7-etheno-1,3,3a,7a-tetrahydro-cyclobut[f]isoindole instead of 1,3-dioxo-2H-4,6-etheno-1,3,3a,6a-tetrahydro-cycloprop[f]isoindole. The compound is converted to the dihydrochloride salt; m.p. 237°–240° C.

Analysis for: $C_{24}H_{33}N_5O_2.2HCl.1\frac{1}{2}H_2O$: Calculated: C, 55.06; H, 7.26; N, 13.38. Found: C, 55.15; H, 6.87; N, 13.34.

EXAMPLE 7

2-[4-[4-(2-Pyrimidinyl)-1-piperazinyl]butyl]octahydro-4,6-ethanoxycloprop[f]isoindole-1,3-(2H, 3aH)-dione, dihydrochloride, dihydrate

The title compound is prepared following the procedure of Example 1 using 1,3-dioxo-2H-4,6-ethano-1,3,3a,5a,6-tetrahydrocycloprop[f]isoindole instead of 1,3-dioxo-2H-4,6-etheno-1,3,3a,6a-tetrahydrocycloprop[f]isoindole and 1-(2-pyrimidinyl)piperazine dihydrochloride instead of 1-(6-chloro-2-pyrazinyl)piperazine hydrochloride. The compound is converted to the dihydrochloride salt; m.p. 190°–192° C.

Analysis for: $C_{23}H_{31}N_5O_2.2HCl.2H_2O$: Calculated: C, 53.24; H, 7.13; N, 13.50. Found: C, 53.41; H, 6.70; N, 13.43.

EXAMPLE 8

2-[4-[4-(6-Chloro-2-pyrazinyl)-1-piperazinyl]butyl]octahydro-4,9-etheno-1H-cycloocta[c]pyrrole-1,3(2H)-dione, dihydrochloride, sesquihydrate

The title compound is prepared following the procedure of Example 1 using octahydro-4,9-etheno-1H-cycloocta[c]pyrrole-1,3(2H)-dione instead of 1,3-dioxo-2H-4,6-etheno-1,3,3a,6a-tetrahydrocycloprop[f]isoindole and is converted to the hydrochloride salt; m.p. 248°–250° C.

Analysis for: $C_{24}H_{32}ClN_5O_2.2HCl.\frac{1}{2}H_2O$: Calculated: C, 51.65; H, 6.80; N, 12.55; Cl, 19.41. Found: C, 51.13; H, 5.70; N, 13.16; Cl, 20.63.

EXAMPLE 9

2-[4-[4-(6-Chloro-3-pyridazinyl)-1-piperazinyl]butyl]-hexahydro-4,6-ethenocycloprop[f]isoindole-1,3-(2H,3H)-dione, hydrochloride

The title compound is prepared following the procedure of Example 1 using 1-(6-chloro-3-pyridazinyl)-piperazine instead of 1-(6-chloro-2-pyrazinyl)-piperazine and is converted to the hydrochloride salt; mp. 271°–273° C.

Analysis for: $C_{23}H_{28}ClN_5O_2.HCl$: Calculated: C, 57.74; H, 6.06; N, 14.64. Found: C, 57.61; H, 6.01; N, 14.30.

EXAMPLE 10

2-[4-[4-(3-Chloro-2-pyrazinyl)-1-piperazinyl]butyl]octahydro-4,7-etheno-1H-cyclobut[f]isoindole-1,3(2H)-dione, dihydrochloride, hydrate

The title compound is prepared following the procedure of Example 1 using octahydro-4,7-etheno-1H-cyclobut[f]isoindole-1,3-(2H)-dione instead of hexahydro-4,6-ethenocycloprop[f]isoindole-1,3-(2H,3aH)-dione and 1-(3-chloro-2-pyrazinyl)piperazine instead of 1-(6-chloro-2-pyrazinyl)piperazine; and is converted to the hydrochloride salt; m.p. 208°–210° C.

Analysis for: $C_{24}H_{30}ClN_5O_2.2HCl.H_2O$: Calculated: C, 56.47; H, 6.47; N, 13.72. Found: C, 55.94; H, 6.19; N, 13.43.

EXAMPLE 11

3a,4,4a,6a,7,7a-Hexahydro-2-[4-[4-(6-chloro-3-pyridazinyl-1-piperazinyl]butyl]4,7-etheno-1H-cyclobut[f]isoindole-1,3(2H)-dione, hydrochloride, hydrate

The title compound is prepared following the procedure of Example 1 using 1,3-dioxo-4,7-etheno-Δ$^5$-1,3,3a,7a,-tetrahydrocyclobut[f]isoindole instead of hexahydro-4,6-ethenocycloprop[f]isoindole-1,3-(2H,3aH)-dione and 1-(6-chloro-3-pyridazinyl)-piperazine instead of 1-(6-chloro-2-pyrazinyl)-piperazine; and is converted to the hydrochloride salt; m.p. 282°–283° C.

Analysis for: $C_{24}H_{28}ClN_5O_2.2HCl.H_2O$: Calculated: C, 56.72; H, 6.10; N, 13.78. Found: C, 57.09; H, 5.90; N, 13.61.

EXAMPLE 12

3a,4,4a,6a,7,7a,-Hexahydro-2-[4-[4-(3-chloro-2-pyrazinyl-1-piperazinyl]butyl]4,7-etheno-1H-cyclobut[f]isoindole-1,3(2H)-dione, hydrochloride, dihydrate

The title compound is prepared following the procedure of Example 1 using 1,3-dioxo-4,7-etheno-Δ$^5$-1,3,3a,7a,-tetrahydrocyclobut[f]isoindole instead of hexahydro-4,6-ethenocycloprop[f]isoindole-1,3-(2H,3aH)-dione and 1-(3-chloro-2-pyrazinyl)piperazine instead of 1-(6-chloro-2-pyrazinyl)-piperazine; and is converted to the hydrochloride salt; m.p. 150°–152° C.

Analysis for: $C_{24}H_{28}ClN_5O_2.2HCl.H_2O$: Calculated: C, 54.71; H, 6.77; N, 13.3. Found: C, 54.8; H, 6.35; N, 13.55.

EXAMPLE 13

3a,4,7,7a,-Tetrahydro-2-[4-[4-(6-chloro-2-pyrazinyl)-1-piperazinyl]butyl]-4,7-methano-1H-isoindole hydrochloride hydrate

The title compound is prepared using the procedure of Example 1 using norborn-5-ene-2,3-dicarboximide instead of 1,3-dioxo-2H-4,6-etheno-1,3,3a,6a-tetrahydrocycloprop[f]isoindole and is converted to the hydrochloride salt; mp 235°–237° C.

Analysis for: $C_{21}H_{26}ClN_5O_2.HCl.H_2O$: Calculated: C, 53.61; H, 6.17; N, 14.89. Found: C, 53.04; H, 6.07; N, 15.47.

EXAMPLE 14

2-[4-[4-(6-Chloro-2-pyrazinyl)-1-piperazinyl]butyl]octahydro-4,9-ethano-1H-cycloocta[c]pyrrole-1,3-dione, hydrochloride, hemihydrate

The title compound is prepared following the procedure of Example 1, using octahydro-4,9-ethano-1H-cycloocta[c]pyrrole-1,3(2H)-dione instead of hexahydro-4,6-ethenocycloprop[f]isoindole-1,3(2H,3aH)-dione and is converted to the hydrochloride salt;;m.p. 277°–280° C.

Analysis for: $C_{24}H_{34}ClN_5O_2.HCl.\frac{1}{2}H_2O$: Calculated: C, 57.01; H, 6.93; N, 13.86. Found: C, 56.96; H, 6.30; N, 13.68.

EXAMPLE 15

2-[4-[4-(6-Chloro-2-pyrazinyl)-1-piperazinyl]butyl]-octahydro-4,7-etheno-1H-cyclobut[f]isoindol-1,3-(2H)-dione, hydrochloride

The title compound is prepared following the procedure of Example 1, using octahydro-4,7-etheno-1H-cyclobut[f]isoindole-1,3(2H)-dione instead of hexahydro-4,6-ethenocycloprop[f]isoindole-1,3(2H,3aH)-dione and is converted to the hydrochloride salt; m.p. 268°–271° C.

Analysis for: $C_{24}H_{30}ClN_5O_2.HCl$: Calculated: C, 58.53; H, 6.30; N, 14.22; Cl, 14.43. Found: C, 59.03; H, 6.36; N, 14.12; Cl, 13.86.

EXAMPLE 16

2-[4-[4-(2-Pyrimidinyl)-1-piperazinyl]butyl]-octahydro-4,7-etheno-1H-cyclobut[f]isoindole-1,3-(2H)-dione, dihydrochloride, hydrate

The title compound is prepared following the procedure of Example 1, using 1-(2-pyrimidinyl)piperazine instead of 1-(6-chloro-2-pyrazinyl)piperazine hydrochloride and octahydro-4,7-etheno-1H-cyclobut[f]isoindole-1,3(2H)-dione instead of hexahydro-4,6-ethenocycloprop[f]isoindole-1,3(2H,3aH)-dione and is converted to the hydrochloride salt; m.p. 250°–252° C.

Analysis for: $C_{24}H_{31}N_5O_2.2HCl.H_2O$: Calculated: C, 56.25; H, 6.83; N, 13.67. Found: C, 56.10; H, 6.66; N, 13.67.

EXAMPLE 17

2-[4-[4-(6-Chloro-3-pyridazinyl)-1-piperazinyl]butyl]-3a,4,7,7a-tetrahydro-4,7-methano-1H-isoindole-1,3-(2H)-dione, hydrochloride, dihydrate

The title compound is prepared following the procedure of Example 1, using 1-(6-chloro-3-pyridazinyl)piperazine hydrochloride instead of 1-(6-chloro-2-pyrazinyl)piperazine hydrochloride and 3a,4,7,7a-tetrahydro-4,7-methano-1H-isoindole-1,3(2H)-dione instead of hexahydro-4,6-ethenocycloprop[f]isoindole-1,3(2H,3aH)-dione and is converted to the hydrochloride salt; m.p. 285° C.

Analysis for: $C_{21}H_{26}N_5ClO_2.HCl.2 H_2O$: Calculated: C, 51.64; H, 6.39; N, 14.34. Found: C, 51.28; H, 5.74; N, 14.18.

EXAMPLE 18

2-[4-[4-(3-Chloro-2-pyrazinyl)-1-piperazinyl]butyl]-3a,4,7,7a-tetrahydro-4,7-methano-1H-isoindole-1,3-(2H)-dione, hydrochloride, 2.5 hydrate

The title compound is prepared following the procedure of Example 1, using 1-(3-chloro-2-pyrazinyl)piperazine instead of 1-(6-chloro-2-pyrazinyl)piperazine hydrochloride and 3a,4,7,7a-tetrahydro-4,7-methano-1H-isoindole-1,3(2H)-dione instead of hexahydro-4,6-ethenocycloprop[f]isoindole-1,3-(2H,3aH)-dione and is converted to the hydrochloride salt; m.p. 185°–187° C.

Analysis for: $C_{21}H_{26}N_5O_2Cl.HCl.2.5 H_2O$: Calculated: C, 50.60; H, 6.40; N, 14.07. Found: C, 49.78; H, 5.73; N, 13.97.

EXAMPLE 19

2-[4-[4-(3-Chloro-2-pyrazinyl)-1-piperazinyl]butyl]hexahydro-4,6-ethenocycloprop[f]isoindole-1,3(2H,3aH)-dione, hydrochloride

The title compound is prepared following the procedure of Example 1, using 1-(3-chloro-2-pyrazinyl)piperazine instead of 1-(6-chloro-2-pyrazinyl)piperazine hydrochloride and is converted to the hydrochloride salt; m.p. 110°–112° C.

Analysis for: $C_{23}H_{28}N_5O_2Cl.HCl.H_2O$: Calculated: C, 55.64; H, 6.29; N, 14.11. Found: C, 55.56; H, 6.21; N, 14.16.

EXAMPLE 20

2-[4-[4-(3-Chloro-2-pyrazinyl)-1-piperazinyl]butyl]octahydro-4,9-etheno-1H-cycloocta[c]pyrrole-1,3(2H)-dione, hydrochloride, hydrate

The title compound is prepared following the procedure of Example 1, using octahydro-4,9-etheno-1H-cycloocta[c]pyrrole-1,3(2H)-dione instead of hexahydro-4,6-ethenocycloprop[f]isoindole-1,3(2H,3aH)-dione and 1-(3-chloro-2-pyrazinyl)piperazine instead of 1-(6-chloro-2-pyrazinyl)piperazine hydrochloride and is converted to the hydrochloride salt; m.p. 208°–211° C.

Analysis for: $C_{24}H_{32}ClN_5O_2.HCl.H_2O$: Calculated: C, 56.25; H, 6.83; N, 13.67. Found: C, 55.83; H, 6.23; N, 13.43.

EXAMPLE 21

4,5,6,7,8,8a-Hexahydro-2-[4-[4-(2-pyrimidinyl)-1-piperazinyl]butyl]-4,8-etheno-cyclohepta[c]pyrrole-1,3(2H,3aH)-dione, dihydrochloride, hemihydrate

The title compound is prepared following the procedure of Example 1, using 4,5,6,7,8,8a-hexahydro-4,8-ethenocyclohepta[c]pyrrole-1,3-(2H,3aH)-dione instead of hexahydro-4,7-ethenocycloprop[f]isoindole-1,3-(2H,3aH)-dione and 1-(2-pyrimidinyl)piperazine instead of 1-(6-chloro-2-pyrazinyl)piperazine hydrochloride and is converted to the hydrochloride salt; m.p. 250°–252° C.

Analysis for: $C_{23}H_{31}N_5O_2.2HCl.\frac{1}{2}H_2O$: Calculated: C, 56.21; H, 6.92; N, 14.25; Cl, 14.20. Found: C, 56.69; H, 6.79; N, 14.10; Cl, 14.17.

EXAMPLE 22

2-[4-[4-(6-Chloro-2-pyrazinyl)-1-piperazinyl]butyl]-4,5,6,7,8,8a-hexahydro-4,8-ethenocyclohepta[c]pyrrole-1,3(2H,3aH)-dione, hydrochloride, hydrate

The title compound is prepared following the procedure of Example 1, using 4,5,6,7,8,8a-hexahydro-4,8-ethenocyclohepta[c]pyrrole-1,3-(2H,3aH)-dione instead of hexahydro-4,7-ethenocycloprop[f]isoindole-1,3-(2H,3aH)-dione and is converted to the hydrochloride salt; m.p. 254°–256° C.

Analysis for: $C_{23}H_{30}ClN_5O_2.HCl.H_2O$: Calculated: C, 55.53; H, 6.63; N, 14.08. Found: C, 55.69; H, 6.77; N, 14.88.

EXAMPLE 23

3a,4,4a,6a,7,7a-Hexahydro-2-[4-[4-(2-pyrazinyl)-1-piperazinyl]butyl]-4,7-etheno-1H-cyclobut[f]isoindole-1,3-(2H)-dione, fumarate (1:1)

The title compound is prepared following the procedure of Example 1, using 3a,4,4a,6a,7,7a-hexahydro-4,7-etheno-1H-cyclobut[f]isoindole-1,3(2H)-dione instead of hexahydro-4,7-ethenocycloprop[f]isoindole-1,3-(2H,3aH)-dione and 1-(2-pyrazinyl)piperazine hydrochloride instead of 1-(6-chloro-2-pyrazinyl)piperazine hydrochloride and is converted to the fumarate salt; m.p. 169°–170° C.

Analysis for: $C_{24}H_{29}N_5O_2.C_4H_4O_4$: Calculated: C, 62.80; H, 6.16; N, 13.08. Found: C, 63.00; H, 6.35; N, 13.00.

EXAMPLE 24

4,4a,5,5a,6,6a-Hexahydro-2-[4-[4-(2-pyrazinyl)-1-piperazinyl]butyl]-4,6-ethenocycloprop[f]isoindole-1,3-(2H,3aH)-dione, dihydrochloride, hydrate

The title compound is prepared following the procedure of Example 1, using 1-(2-pyrazinyl)piperazine hydrochloride instead of 1-(6-chloro-2-pyrazinyl)piperazine hydrochloride and is converted to the hydrochloride salt; m.p. 200°–202° C.

Analysis for: $C_{23}H_{29}N_5O_2 \cdot 2HCl \cdot H_2O$: Calculated: C, 55.42; H, 6.67; N, 14.05; Cl, 14.23. Found: C, 55.38; H, 6.67; N, 13.86; Cl, 14.30.

EXAMPLE 25

2-[4-[4-(6-Chloro-2-pyrazinyl)-1-piperazinyl]butyl]hexahydro-4,6-ethanocycloprop[f]isoindole-1,3-(2H,3aH)-dione, hydrochloride The title compound is prepared following the procedure of Example 1 using hexahydro-4,6-ethanocycloprop[f]isoindole-1,3(2H,3aH)-dione instead of hexahydro-4,7-ethenocycloprop[f]isoindole-1,3(2H,3aH)-dione and is converted to the hydrochloride salt; m.p. 266°–268° C.

Analysis for: $C_{23}H_{30}ClN_5O_2 \cdot HCl$: Calculated: C, 57.50; H, 6.45; N, 14.58; Cl, 14.79. Found: C, 57.33; H, 6.75; N, 14.08; Cl, 14.40.

EXAMPLE 26

2-[4-[4-(3-Chloro-2-pyrazinyl)-1-piperazinyl]butyl]hexahydro-4,6-ethanocycloprop[f]isoindole-1,3(2H,3aH)-dione, hydrochloride The title compound is prepared following the procedure of Example 1, using hexahydro-4,6-ethanocycloprop[f]isoindole-1,3-(2H,3aH)-dione instead of hexahydro-4,7-ethenocycloprop[f]isoindole-1,3(2H,3aH)-dione and 1-(3-chloro-2-pyrazinyl)piperazine instead of 1-(6-chloro-2-pyrazinyl)piperazine hydrochloride and is converted to the hydrochloride salt; m.p. 245°–246° C.

Analysis for: $C_{23}H_{30}ClN_5O_2 \cdot HCl$: Calculated: C, 57.50; H, 6.45; N, 14.58; Cl, 14.79. Found: C, 57.38; H, 6.12; N, 14.21; Cl, 15.50.

EXAMPLE 27

3a,4,4a,5,6,6a,7,7a-Octahydro-2-[4-[4-(2-pyrazinyl)-1-piperazinyl]butyl]-4,7-etheno-1H-cyclobut[f]isoindole-1,3(2H)-dione, dihydrochloride, hemihydrate The title compound is prepared following the procedure of Example 1, using 3a,4,4a,5,6,6a,7,7a-octahydro-4,7-etheno-1H-cyclobut[f]isoindole-1,3(2H)-dione instead of hexahydro-4,7-ethenocycloprop[f]isoindole-1,3(2H,3aH)-dione and 1-(2-pyrazinyl)piperazine hydrochloride instead of 1-(6-chloro-2-pyrazinyl)piperazine hydrochloride and is converted to the hydrochloride salt; m.p. 208°–210° C.

Analysis for: $C_{24}H_{31}N_5O_2 \cdot 2HCl \cdot \frac{1}{2}H_2O$: Calculated: C, 57.25; H, 6.75; N, 13.91. Found: C, 57.12; H, 6.88; N, 13.86.

EXAMPLE 28

3a,4,4a,6a,7,7a-Hexahydro-2-[4-[4-(5-trifluoromethyl-2-pyridinyl)-1-piperazinyl]butyl]-4,7-etheno-1H-cyclobut[f]isoindole-1,3(2H)-dione, dihydrochloride, hydrate The title compound is prepared following the procedure of Example 1, using 3a,4,4a,6a,7,7a-hexahydro-4,7-etheno-1H-cyclobut[f]isoindole-1,3(2H)-dione instead of hexahydro-4,7-ethenocycloprop[f]isoindole-1,3(2H,3aH)-dione and 1-(5-trifluoromethyl-2-pyridinyl)piperazine hydrochloride instead of 1-(6-chloro-2-pyrazinyl)piperazine hydrochloride and is converted to the hydrochloride salt; m.p. 233°–235° C.

Analysis for: $C_{26}H_{29}F_3N_4O_2 \cdot 2HCl \cdot H_2O$: Calculated: C, 54.03; H, 5.71; N, 9.69. Found: C, 54.17; H, 5.58; N, 9.86.

EXAMPLE 29

4,5,6,7,8,8a-Hexahydro-2-[4-[4-(2-pyrimidinyl)-1-piperazinyl]butyl]-4,8-ethanocyclohepta[c]pyrrole-1,3(2H,3aH)-dione, dihydrochloride The title compound is prepared following the procedure of Example 1, using 4,5,6,7,8,8a-hexahydro-4,8-ethanocyclohepta[c]pyrrole-1,3-(2H,3aH)-dione instead of hexahydro-4,7-ethenocycloprop[f]isoindole-1,3-(2H,3aH)-dione and 1-(2-pyrimidinyl)piperazine instead of 1-(6-chloro-2-pyrazinyl)piperazine hydrochloride and is converted to the hydrochloride salt; m.p. 209°–211° C.

Analysis for: $C_{23}H_{33}N_5O_2 \cdot 2HCl$: Calculated: C, 57.02; H, 7.23; N, 14.46. Found: C, 57.74; H, 7.23; N, 14.50.

EXAMPLE 30

2-[4-[4-(3-Chlorophenyl)-1-piperazinyl]butyl]-3a,4,4a,6a,7,7a-hexahydro-4,7-etheno-1H-cyclobut[f]isoindole-1,3(2H)-dione, dihydrochloride A mixture of an equimolar quantity of 3a,4,4a,6a,7,7a-hexahydro-4,7-ethanocyclobut[f]isobenzofuran-1,3-dione and 1-(4-aminobutyl)-4-(3-chlorophenyl)piperazine in pyridine is refluxed overnight. Pyridine is removed under reduced pressure and the resulting solid is recrystallized from an ethanol-ethyl acetate (1:2) mixture to afford the title compound, which is converted to the dihydrochloride salt by dissolving the free base in ethanol and adding ether saturated with hydrogen chloride; m.p. 225°–227° C.

Analysis for: $C_{26}H_{30}N_3ClO_2 \cdot 2HCl$: Calculated: C, 59.48; H, 6.1; N, 8.0. Found: C, 59.43; H, 6.23; N, 8.01.

EXAMPLES 31–35

The following compounds are prepared by reacting the appropriate polycyclic diacid anhydride with the appropriately substituted aryl- or heteroarylpiperazinylbutylamine as described in Example 30. In the event that suitable substituted butylamines are not easily accessible, the desired compounds can be prepared via the reaction of polycyclic halobutyl imides with the appropriate aryl- or heteroarylpiperazines as described in Example 1.

EXAMPLE 31

4,4a,5,5a,6,6a-Hexahydro-2-[4-[4-[3-(trifluoromethyl)-phenyl]-1-piperazinyl]butyl]-4,6-ethenocycloprop[f]-isoindole-1,3(2H,3aH)-dione, dihydrochloride, hemihydrate Melting point: 218°–220° C.

Analysis for: $C_{26}H_{30}F_3N_3O_2 \cdot 2HCl \cdot \frac{1}{2}H_2O$: Calculated: C, 56.21; H, 5.94; N, 7.56. Found: C, 56.13; H, 5.69; N, 7.34.

EXAMPLE 32

3a,4,4a,6a,7,7a-Hexahydro-2-[4-[4-[3-(trifluoromethyl)-phenyl]-1-piperazinyl]-butyl]-4,7-etheno-1H-cyclobut[f]isoindole-1,3(2H)-dione, dihydrochloride Melting point: 227°–228° C.

Analysis for: $C_{27}H_{30}F_3N_3O_2 \cdot 2HCl$: Calculated: C, 58.06; H, 5.73; N, 7.52; Cl, 12.72. Found: C, 58.15; H, 5.75; N, 7.60; Cl, 12.33.

EXAMPLE 33

4,4a,5,5a,6,6a-Hexahydro-2-[4-[4-(2-methoxyphenyl)-1-piperazinyl]butyl]-4,6-ethenocycloprop[f]isoindole-1,3(2H,3aH)-dione, dihydrochloride Melting point: 210°–213° C.
Analysis for: $C_{26}H_{33}N_3O_3 \cdot 2HCl$: Calculated: C, 61.41; H, 6.88; N, 8.26. Found: C, 60.94; H, 6.88; N, 8.26.

EXAMPLE 34

3a,4,4a,6a,7,7a-Hexahydro-2-[4-[4-(2-methoxyphenyl)-1-piperazinyl]butyl]-4,7-etheno-1H-cyclobut[f]isoindole-1,3(2H)-dione, dihydrochloride, hemihydrate Melting point: 233°–235° C.
Analysis for: $C_{27}H_{33}N_3O_3 \cdot 2HCl \cdot \frac{1}{2}H_2O$: Calculated: C, 61.24; H, 6.81; N, 7.93. Found: C, 61.52; H, 6.93; N, 7.87.

EXAMPLE 35

4,4a,5,5a,6,6a-Hexahydro-2-[4-[4-(3-chlorophenyl)-1-piperazinyl]butyl]-4,6-ethenocycloprop[f]isoindole-1,3(2H,3aH)-dione, dihydrochloride, hemihydrate Melting point: 212°–213° C.
Analysis for: $C_{25}H_{30}ClN_3O_2 \cdot 2HCl \cdot \frac{1}{2}H_2O$: Calculated: C, 57.52; H, 6.32; N, 8.05. Found: C, 57.80; H, 6.16; N, 7.95.

EXAMPLE 36

The compounds of the invention are tested in an assay to determine their ability to antagonise apomorphine-induced stereotyped behavior. The assay measures the in vivo dopamine reception blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80® in water, are administered at several dose levels to male mice (6/dose level). A control group, run simultaneously with drug groups, receives equal volumes of solvent. Thirty minutes later (i.p. administration) or 60 minutes later (p.o. administration), drug-treated and control mice are challenged with 10 mg/kg apormorphine s.c.. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| Standard Compounds: | $ED_{50}$ and 95% confidence interval mg/kg intraperitoneal |
|---|---|
| Haloperidol | 1.37 (0.88–2.34) |
| Chloropromazine | 8.48 (4.79–16.38) |
| Clozapine | 30.06 (19.42–48.21) |

The compounds of the invention, when tested in this assay are inactive, evidencing a low potential for exhibiting extrapyramidal side effects, such as pseudo parkinsonism, tardive dyskinesia and the like.

EXAMPLE 37

The compounds of the invention are further studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The test is carried out as follows:

Several rats are decapitated and the brains are rapidly removed. Limbic brain tissue (nucleus accumbens, septal area, olfactory tubercle) is dissected and homogenized on ice in 9 volumes of buffer (50 mM Tris-HCl, 120 mM NaCl, 5 mM KCl, 1 mM $CaCl_2$, 1 mM $MgCl_2$, 0.1% L-ascorbic acid, 10 $\mu$M pargyline HCl, pH 7.1) using a Polytron homogenizer at setting 5 for three 15-sec bursts. The homogenate is then diluted 4-fold with buffer and centrifuged at 30,000× g for 20 minutes, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty $\mu$L of the homogenate (0.2–0.3 mg protein/sample) are incubated with 0.3 nM $^3$H-spiroperidol (New England Nuclear) and various concentrations of test drug in a final volume of 1 ml of the above buffer for 10 minutes in a 37° C. water bath. At the end of the incubation, 3 ml of cold 50 mM Tris-HC-1, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 minutes with 10 ml of Hydrofluor (National Diagnostics) scintillation cocktail. The vials are then counted in a Packard 460CD scintillation counter.

Specific binding is defined as total binding less binding in the presence of 1$\mu$M (+)butaclamol. Binding in the presence of various concentrations of test drug is expressed as a per cent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-Spiroperidol}]}{K_D}} \quad \text{where } K_D = 0.3 \text{ nM for spiroperidol binding}$$

| Standard Compounds: | $K_i$ and 95% confidence interval |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention, and the prior art compound buspirone (8-[4-[4-(2-pyrimidinyl)-1-piperazinyl]-butyl]-8-azapiro[4.5]-decane-7,9-dione) in this assay are presented in Table 1.

TABLE 1

| Compound of Example No. | Limbic D-2 Binding ($K_i$nM) |
|---|---|
| Buspirone | 119 |
| 1 | 690 |
| 3 | 345 |
| 7 | 140 |
| 8 | 345 |
| 13 | 1% inhibition at 1 μM |
| 14 | 440 |
| 15 | 413 |
| 16 | 85 |
| 17 | 19% inhibition at 1 μM |
| 18 | 48% inhibition at 1 μM |
| 19 | 54 |
| 20 | 78% inhibition at 1 μM |
| 21 | 53% inhibition at 1 μM |
| 22 | 43% inhibition at 1 μM |
| 23 | 13% inhibition at 1 μM |
| 24 | 38% inhibition at 1 μM |
| 25 | 49% inhibition at 1 μM |
| 26 | 75% inhibition at 1 μM |
| 27 | 41% inhibition at 1 μM |
| 30 | 3% inhibition at 1 μM |
| 31 | 91% inhibition at 1 μM |
| 32 | 96% inhibition at 1 μM |
| 33 | 16% inhibition at 1 μM |
| 34 | 100% inhibition at 1 μM |
| 35 | 100% inhibition at 1 μM |

The results show that compounds of the invention display a very weak effect, evidencing a low potential for extrapyramidal side effects. In this regard it should be noted, nevertheless, that while some compounds do show a high affinity for the D-2 receptor site, they also demonstrate a high affinity for $5\text{-HT}_{1A}$ receptor sites, as can be seen from the data in Example 40, below.

EXAMPLE 38

The antipsychotic activity of the compounds of the invention is assessed via the conditioned avoidance (discrete trial) test. This test has excellent clinical correlation for antipsychotic activity.

The test is carried out as follows:

Male CD rats (Charles River) maintained at approximately 400–450 gm body weight are used. Rats trained previously are placed in plexiglass experimental chambers equipped with a response lever, house light, and sonalert. A steel grid floor is wired for presentation of electric shock. Each trial consists of a fifteen-second warning tone (conditioned stimulus), continuing for an additional fifteen seconds accompanied by electric shock, (unconditioned stimulus). The rat can terminate a trial at any point by depression of the response lever. As response during the initial fifteen-second warning tone ends the trial before shock delivery and is considered avoidance response, while a response occurring during shock delivery is an escape response. Trials are presented on a variable interval schedule of two minutes. The session consists of sixty trials. Animals are run two to three times weekly with control sessions always preceding a drug run, and with at least one day intervening, compounds are administered i.p. or p.o. at appropriate pretreatment times to a minimum of five to six rats at each dose level over a range of doses.

The following experimental parameters are recorded by computer: (1) the number of interval responses, (2) the number of avoidance responses, (3) the number of escape responses, and (4) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential antipsychotic compounds suppress avoidance responding and increase escape responding.

| STANDARD COMPOUNDS | $AB_{50}$ (mg/kg i.p.) |
|---|---|
| Spiperone | 0.13 |
| Haloperidol | 0.18 |
| Chloropromazine | 2.50 |
| Thioridazine | 8.61 |
| Clozapine | 10.82 |

The results for compounds of this invention in this test are presented in Table 2.

TABLE 2

| Compound of Example No. | Active at mg/kg |
|---|---|
| 1 | 40 (p.o.)*[1] |
| 2 | 40 (i.p.)** |
| 3 | 13.4 (p.o.)[1] |
| 6 | 40 (p.o.) |
| 13 | 39.7 (p.o.)[1] |
| 15 | 40 (p.o.) |
| 16 | 47.4 (p.o.)[1] |
| 17 | 40 (p.o.) |
| 18 | 40 (p.o.)[1] |
| 20 | 40 (p.o.) |
| 22 | 68.4 (p.o.)[1] |
| 23 | 40 (p.o.) |
| 24 | 49.58 (p.o.)[1] |
| 25 | 40 (p.o.) |
| 26 | 40 (p.o.) |
| 27 | 40 (p.o.) |
| 28 | 40 (p.o.) |
| 30 | 40 (i.p.) |
| 31 | 44 (p.o.)[1] |
| 32 | 40 (p.o.)[1] |
| 33 | 40 (i.p.) |
| 34 | 19 (p.o.)[1] |
| 35 | 40 (i.p.) |

*(p.o.) = perorally administered drug.
**(i.p.) = intraperitoneally administered drug.
[1] = $AB_{50}$ value The results show that compounds of the invention have significant oral activity in the test procedure employed.

EXAMPLE 39

Another test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber (10½"×6¾"×11⅞" high) and an elevated chamber or shelf (5⅜"×6⅜"×5¾"). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock, (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential antipsychotic compounds suppress avoidance responding and increase escape responding.

| Standard Compounds: | $AB_{50}$ (mg/kg i.p.) |
| --- | --- |
| Haloperidol | 0.19 |
| Chlorpromazine | 3.69 |
| Clozapine | 6.94 |
| Buspirone | 9.94 |

The results for compounds of this invention in this test are presented in Table 3.

TABLE 3

| Compound of Example No. | Active at mg/kg |
| --- | --- |
| 1 | 40 (i.p.)* |
| 2 | 40 (i.p.) |
| 3 | 40 (i.p.) |
| 4 | 40 (i.p.) |
| 5 | 40 (i.p.) |
| 6 | 40 (i.p.) |
| 7 | 40 (i.p.) |
| 8 | 40 (i.p.) |
| 9 | 40 (i.p.) |
| 10 | 40 (i.p.) |
| 11 | 40 (i.p.) |
| 12 | 40 (i.p.) |
| 13 | 40 (i.p.) |
| 14 | 40 (i.p.) |
| 15 | 40 (i.p.) |
| 16 | 40 (i.p.) |
| 17 | 40 (i.p.) |
| 18 | 40 (i.p.) |
| 19 | 40 (i.p.) |
| 20 | 40 (i.p.) |
| 21 | 40 (i.p.) |
| 22 | 40 (i.p.) |
| 23 | 40 (i.p.) |
| 24 | 40 (i.p.) |
| 25 | 40 (i.p.) |
| 26 | 40 (i.p.) |
| 27 | 40 (i.p.) |
| 28 | 40 (i.p.) |
| 29 | 40 (i.p.) |
| 30 | 40 (i.p.) |
| 31 | 40 (i.p.) |
| 32 | 40 (i.p.) |
| 33 | 40 (i.p.) |
| 34 | 40 (i.p.) |
| 35 | 40 (i.p.) |

*(i.p.) = intraperitoneally administered drug.

The results show that compounds of the invention are active intraperitoneally in this test.

EXAMPLE 40

The ex vivo inhibition of 5-HT-1A serotonin receptor binding assay is used to determine whether the test compounds can cross the blood-brain barrier and affect the receptor in question and to give an indication of buspirone-like anxiolytic activity.

The assay is carried out as follows:

Several groups of rats (4-6 rats/group) are injected with test compound or the appropriate vehicle. Thirty minutes later, unless otherwise noted, rats are decapitated and their brains removed. Various brain regions are dissected and rapidly frozen and maintained at −70° C. until used.

Hippocampal tissue is dissected and homogenized on ice in 40 vols of buffer (50 mM Tris HCl,pH=7.7) using a Polytron homogenizer at setting 5 for 3×15 sec bursts. The homogenate is then centrifuged at 20,000 rpm (RC5-B; 50,000 g) and the supernatant discarded. The pellet is resuspended in 40 vols of the same buffer and incubated at 37° C. for 10 minutes to aid in the removal of endogenous serotonin. The homogenate is then centrifuged (as above) and the supernatant discarded. The pellet is then resuspended in 100 vols of buffer B (50 mM Tris HCl, pH=7.7 containing 0.1% ascorbate, 10 μM pargyline and 4 mM $CaCl_2$) and sonicated. An aliquot is taken for protein determination by the Lowry method and the remainder stored frozen at −70° C. until used.

The homogenate (50 μl; 0.4-0.6 mg protein/sample) is incubated with 100 μl (1.5-1.8 nM) $^3$H-8-hydroxy-2-(di-n-propylamino)tetraline in a final volume of 2 ml of buffer for 10 minutes at 37° C. At the end of the incubation, 3 ml of cold buffer A are added to each tube, and the contents rapidly filtered through Whatman GF/B glass filters. The filters are then rapidly washed 2 times with 3 ml of the same buffer, placed in scintillation vials, and shaken for 15 minutes with 10 ml of Hydrofluor (National Diagnostics) scintillation cocktail. The vials are then counted in a Packard 460CD scintillation counter.

Specific binding is calculated for each of the treatment protocols and is defined as total binding less binding in the presence of excess unlabeled serotonin (1 μM). Specific binding obtained in vehicle-treated rats is compared to that obtained in animals receiving a single or various doses of test compound and expressed as percent of control. These results are then plotted as logit % binding vs. log concentration of test drug. Linear regression analysis then yields a straight line with 95% confidence limits from which an IC$_{50}$ can be inversely predicted. K$_i$ (inhibition constant) for the test drug is then calculated by the formula:

$$K_i = \frac{IC_{50}}{1 + \frac{[^3H\text{-}8\text{-}OH\ DPAT]}{K_D}}$$

where $K_D$ = 1.8 nm for 8-OH DPAT binding in hippocampus

The use of several doses of test compound also permits the calculation of an ID$_{50}$ value, i.e. an inhibitory dose that displaces 50% of the specific binding ex vivo.

Under these conditions, buspirone (30 mg/kg) displaced 46% of specific $^3$H-8-OH-DPAT binding from hippocampal membranes.

When tested in this assay, the compounds of the invention gave the following results.

TABLE 4

| Compound of Example No. | Inhibition Constant (K$_i$ nm) |
|---|---|
| 1 | 162 |
| 3 | 17 |
| 7 | 13.9 |
| 8 | 122 |
| 13 | 74% inhibition at 1 μm |
| 16 | 1.1 |
| 21 | 12 |
| 22 | 107 |
| 23 | 46% inhibition at 1 μm |
| 24 | 68% inhibition at 1 μm |
| 27 | 41 |
| 30 | 41 |
| 31 | 26 |
| 32 | 25 |
| 33 | 1.3 |
| 34 | 1.3 |
| 35 | 14 |

The results show that compounds of the invention have a moderate to extremely strong affinity for binding to the 5-HT-1A receptor, site, evidencing a high potential for anxiolytic activity.

EXAMPLE 41

The compounds of the invention are tested in the serotonin syndrome assay which examines the postsynaptic efficacy of compounds with a high affinity for the 5-HT$_{1A}$ receptor subtype.

This assay is carried out as follows:

200–300 g male Sprague Dawley CD rats (Charles River) are housed in groups of 6; food and water are available ad libitum.

Four rats are placed individually into plexiglass observation cages with a layer of bedding covering the bottom. Test compounds and vehicle are administered IP 15 minutes prior to 3 mg/kg IP 5-methoxy-N,N-dimethyltryptamine (5-MeODMT). During the 15 minute pretreatment, subjects are scored for the presence of the 5-HT syndrome (agonist activity). After the 5-MeODMT injection, all subjects are scored for an additional 15 minutes to identify antagonist activity. For initial screening of a compound, a dose of 17 mg/kg may be used. Once the compound is determined to be active, a dose-response curve is generated using 0, 1, 3, 10 and 30 mg/kg doses.

Scoring the 5-HT syndrome consists of rating the following behaviors: (1) forepaw treading, (2) headweaving, (3) tremor, (4) hindlimb abduction, (5) flattened body posture, and (6) Straub tail on a 4-point ranked intensity scale; maximum score is 18. Rats displaying 4 out of 6 symptoms are considered as having the serotonin syndrome.

Results are presented as mean total score (± SEM) for induction of syndrome and for antagonism of syndrome. Student's T-Test is used to compare drug and vehicle results. If a dose-response curve is obtained, ED$_{50}$ values are determined using a nonlinear regression analysis with inverse prediction. Maximum scores of different compounds are compared using the Z test (Standard Normal Statistics) to assess partial agonist activity.

| REFERENCE COMPOUNDS: | | | |
|---|---|---|---|
| Compound | Route | Production of Syndrome ED$_{50}$ (95% CI) mg/kg | Antagonism of Syndrome ED$_{50}$ (95% CI) mg/kg |
| MeODMT | IP | 1.5 (1.1–2.1) | — |
| DPAT | IP | 1.2 (0.7–2.2) | — |
| Buspirone | IP | 7.3 (3.4–15.8) | 4.6 (3.4–6.2) |
| Gepirone | IP | 3.7 (2.7–5.1) | 3.1 (1.4–6.8) |
| Ipsapirone | IP | 5.3 (3.1–9.2) | 5.7 (3.3–9.9) |
| BMY-7378 | IP | no significant effect | 2.8 (1.5–5.2) |

When tested in this assay, a compound of the invention gave the following result, evidencing a significant antagonist activity:

| Compound of Example No. | Production of Syndrome ED$_{50}$ (95% CI) mg/kg | Antagonism of Syndrome ED$_{50}$ (95% CI) mg/kg |
|---|---|---|
| 3 | no significant effect | 3.4 (0.8–13.9) |

What is claimed is:

1. A compound having the formula:

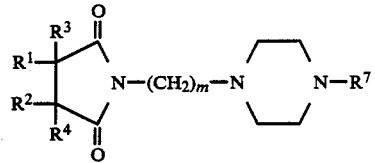

wherein

R$^1$ and R$^2$ represent the structure:

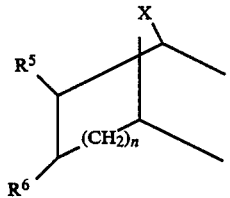

R$^3$ and R$^4$ are hydrogen;
R$^5$ and R$^6$ are hydrogen, or R$^5$ and R$^6$ taken together form a 3–6 membered carbocyclic ring or a cyclobutenyl ring; with the proviso that when R$^3$, R$^4$, R$^5$ and R$^6$ are hydrogen, n is other than zero;
m is 2–4;
n is 0–4;
X is lower alkylene, vinylene or O;
R$^7$ is unsubstituted or monosubstituted phenyl, 2-pyridinyl, 2-pyrimidinyl, 2-pyrazinyl or 3-pyridazinyl; where the substituents are selected from the group lower alkyl, lower alkoxy, halo, cyano, nitro and trifluoromethyl;
and the pharmaceutically acceptable salts thereof.

2. The compound of claim 1, having the name 2-[4-[4-(6-chloro-2-pyrazinyl)-1-piperazinyl]butyl]hexahydro-4,6-ethenocycloprop[f]isoindole-1,3-(2H,3aH)-dione.

3. The compound of claim 1, having the name 4,4a,5,5a,6,6a-hexahydro-2-[4-[4-(2-pyrimidinyl)-1-piperazinyl]butyl]-4,6-ethenocycloprop[f]isoindole-1,3-(2H,3aH)-dione.

4. The compound of claim 1, having the name 3a,4,4a,6a,7,7a-hexahydro-2-[4-[4-(2-pyrimidinyl)-1-piperazinyl]butyl]-4,7-etheno-1H-cyclobut[f]isoindole-1,3-(2H)-dione.

5. The compound of claim 1, having the name 3a,4,4a,6a,7a-hexahydro-2-[4-[4-(6-chloro-2-pyrazinyl)-1-piperazinyl]butyl]-4,7-etheno-1H-cyclobut[f]isoindole-1,3(2H)-dione.

6. The compound of claim 1, having the name 2-[4-[4-(6-chloro-2-pyrazinyl)-1-piperazinyl]butyl]octahydroo-4,7-ethano-1H-cyclobut[f]isoindole-1,3(2H)-dione.

7. The compound of claim 1, having the name 2-[4-[4-(2-pyrimidinyl)-1-piperazinyl]butyl]octahydro-4,7-ethano-1H-cyclobut[f]isoindole-1,3-(2H)-dione.

8. The compound of claim 1, having the name 2-[4-[4-(2-pyrimidinyl)-1-piperazinyl]butyl]octahydro-4,6-ethanocycloprop[f]isoindole-1,3-(2H,3aH)-dione.

9. The compound of claim 1, having the name 2-[4-[4-(6-chloro-2-pyrazinyl)-1-piperazinyl]butyl]octahydro-4,9-etheno-1H-cycloocta[c]pyrrole-1,3-(2H)-dione.

10. The compound of claim 1, having the name 2[4-[4-(6-chloro-3-pyridazinyl)-1-piperazinyl]butyl]hexahydro-4,6-ethenocycloprop[f]isoindole-1,3-(2H,3H)-dione.

11. The compound of claim 1, having the name 2-[4-[4-(3-chloro-2-pyrazinyl)-1-piperazinyl]butyloctahydro-4,7etheno-1H-cyclobut[f]isoindole-1,3-(2H)-dione.

12. The compound of claim 1, having the name 3a,4,4a,6a,7,7a-hexahydro-2-[4-[4-(6-chloro-3-pyridazinyl)-1-piperazinyl]butyl]-4,7-etheno-1H-cyclobut[f]-isoindole-1,3-(2H)-dione.

13. The compound of claim 1, having the name 3a,4,4a,6a,7,7a-hexahydro-2-[4-[4-(3-chloro-2-pyrazinyl)-1-piperazinyl]butyl]-4,7-etheno-1H-cyclobut[f]isoindole-1,3-(2H)-dione.

14. The compound of claim 1, having the name 2-[4-[4-(6-chloro-2-pyrazinyl)-1-piperazinyl]butyl]octahydro-4,9-ethano-1H-cycloocta[c]pyrrole-1,3-(2H)-dione.

15. The compound of claim 1, having the name 2-[4-[4-(6-chloro-2-pyrazinyl)-1-piperazinyl]butyl]-octahydro-4,7-etheno-1H-cyclobut[f]isoindol-1,3-(2H)-dione.

16. The compound of claim 1, having the name 2-[4-[4-(2-pyrimidinyl)-1-piperazinyl]butyl]-octahydro-4,7-etheno-1H-cyclobut[f]isoindole-1,3-(2H)-dione.

17. The compound of claim 1, having the name 2-[4-[4-(6-chloro-3-pyridazinyl)-1-piperazinyl]butyl]-3a,4,7,7a-tetrahydro-4,7-methano-1H-isoindole-1,3-(2H)-dione.

18. The compound of claim 1, having the name 2-[4-[4-(3-chloro-2-pyrazinyl)-1-piperazinyl]butyl]hexahydro-4,6-ethenocycloprop[f]isoindole-1,3-(2H,3aH)-dione.

19. The compound of claim 1, having the name 2-[4-[4-(3-chloro-2-pyrazinyl)-1-piperazinyl]butyl]octahydro-4,9-etheno-1H-cycloocta[c]pyrrole-1,3(2H)-dione.

20. The compound of claim 1, having the name 4,5,6,7,8,8a-hexahydro-2-[4-[4-(2-pyrimidinyl)-1-piperazinyl]butyl]-4,8-ethenocyclohepta[c]pyrrole-1,3-(2H,3aH)-dione.

21. The compound of claim 1, having the name 2-[4-[4-(6-chloro-2-pyrazinyl)-1-piperazinyl]butyl]-4,5,6,7,8,8a-hexahydro-4,8-ethenocyclohepta[c]pyrrole-1,3(2H,3aH)-dione.

22. The compound of claim 1, having the name 3a,4,4a,6a,7,7a-hexahydro-2-[4-[4-(2-pyrazinyl)-1-piperazinyl]butyl]-4,7-etheno-1H-cyclobut[f]isoindole-1,3-(2H)-dione.

23. The compound of claim 1, having the name 4,4a,5,5a,6,6a-hexahydro-2-[4-[4-(2-pyrazinyl)-1-piperazinyl]butyl]-4,6-ethenocycloprop[f]isoindole-1,3-(2H,3aH)-dione.

24. The compound of claim 1, having the name 2-[4-[4-(6-chloro-2-pyrazinyl)-1-piperazinyl]butyl]hexahydro-4,6-ethanocycloprop[f]isoindole-1,3-(2H,3aH)-dione.

25. The compound of claim 1, having the name 2-[4-[4-(3-chloro-2-pyrazinyl)-1-piperazinyl]butyl]hexahydro-4,6-ethanocycloprop[f]isoindole-1,3-(2H,3aH)-dione.

26. The compound of claim 1, having the name 3a,4,4a,5,6,6a,7,7a-octahydro-2-[4-[4-(2-pyrazinyl)-1-piperazinyl]butyl]-4,7-etheno-1H-cyclobut[f]isoindole-1,3(2H)-dione.

27. The compound of claim 1, having the name 3a,4,4a,6a,7,7a-hexahydro-2-[4-[4-(5-trifluoromethyl-2-pyridinyl)-1-piperazinyl]butyl]-4,7-etheno-1H-cyclobut[f]isoindole-1,3(2H)-dione.

28. The compound of claim 1, having the name 4,5,6,7,8,8a-hexahydro-2-[4-[4-(2-pyrimidinyl)-1-piperazinyl]butyl]-4,8-ethanocyclohepta[c]pyrrole-1,3-(2H,3aH)-dione.

29. The compound of claim 1, having the name 2-[4-[4-(3-chlorophenyl)-1-piperazinyl]butyl]-3a,4,4a,6a,7,7a-hexahydro-4,7-etheno-1H-cyclobut[f]isoindole-1,3(2H)-dione.

30. The compound of claim 1, having the name 4,4a,5,5a,6,6a-hexahydro-2-[4-[4-[3-(trifluoromethyl)phenyl]-1-piperazinyl]butyl]-4,6-ethenocycloprop[f]isoindole-1,3(2H,3aH)-dione.

31. The compound of claim 1, having the name 3a,4,4a,6a,7,7a-hexahydro-2[4-[4-[3-(trifluoromethyl)phenyl]-1-piperazinyl]butyl]-4,7-etheno-1H-cyclobut[f]isoindole-1,3(2H)-dione.

32. The compound of claim 1, having the name 4,4a,5,5a,6,6a-hexahydro-2-[4-[4-(2-methoxyphenyl)-1-piperazinyl]butyl]4,6-ethenocycloprop[f]isoindole-1,3(2H,3aH)-dione.

33. The compound of claim 1, having the name 3a,4,4a,6a,7,7a-hexahydro-2-[4-[4-(2-methoxyphenyl)-1-piperazinyl]butyl]-4,7-etheno-1H-cyclobut[f]isoindole-1,3(2H)-dione.

34. The compound of claim 1, having the name 4,4a,5,5a,6,6a-hexahydro-2-[4-[4-(3-chlorophenyl)-1-piperazinyl]butyl]-4,6-ethenocycloprop[f]isoindole-1,3-(2H,3aH)-dione.

* * * * *